United States Patent [19]

Northeved et al.

[11] 4,439,037
[45] Mar. 27, 1984

[54] PROCESS FOR OPTICALLY DETERMINING THE MEAT-TO-LARD-RATIO IN FOR INSTANCE SLAUGHTERED ANIMALS

[75] Inventors: Allan Northeved, Farum; Ole Nilsson, Olstykke, both of Denmark

[73] Assignee: Medicoteknisk Institut, Svejsecentralen, Glostrup, Denmark

[21] Appl. No.: 273,873

[22] PCT Filed: Dec. 6, 1979

[86] PCT No.: PCT/DK79/00056

§ 371 Date: Jul. 9, 1980

§ 102(e) Date: Jul. 9, 1980

[87] PCT Pub. No.: WO80/01205

PCT Pub. Date: Jun. 12, 1980

[30] Foreign Application Priority Data

Dec. 8, 1978 [DK] Denmark ............................ 5546/78

[51] Int. Cl.³ ........................ G01J 3/46; G01N 21/84
[52] U.S. Cl. .................................... 356/402; 356/445
[58] Field of Search ...................... 356/445, 402, 416

[56] References Cited

U.S. PATENT DOCUMENTS 3,224,320 12/1965 Knudsen ............................. 356/256
3,877,818 4/1975 Button et al. ....................... 356/445
4,226,540 10/1980 Barten et al. ....................... 356/445

FOREIGN PATENT DOCUMENTS 2523956 1/1976 Fed. Rep. of Germany ...... 356/445
1193844 6/1970 United Kingdom ................ 356/402

Primary Examiner—Vincent P. McGraw
Attorney, Agent, or Firm—Ladas & Parry

[57] ABSTRACT

By a process for optically determining the meat-to-lard-ratio in for instance slaughtered animals, a probe is inserted perpendicular to the surface of the animal. This probe (7) comprises at least two light fibres (1, 2) opening on to the surface of the probe and communicating at the opposite end with means for transmitting and receiving red light of a predetermined wave length. The signals received are measured relative to a reference value automatically determined as the mean value of the lowest reflection values. This process is so sensitive that even the degree of marbling may be measured.

2 Claims, 3 Drawing Figures

No. 4,439,037

PROCESS FOR OPTICALLY DETERMINING THE MEAT-TO-LARD-RATIO IN FOR INSTANCE SLAUGHTERED ANIMALS

TECHNICAL FIELD

The invention relates to a process for optically determining the meat-to-lard-ratio in objects such as slaughtered animals or portions thereof, by which process a probe with light conducting means in the form of at least one transmitter transmitting light of a predetermined colour and at least one receiver, is inserted substantially perpendicular to the surface of the object.

BACKGROUND ART

Probes of the above type are known. These probes are, however, not so sensitive that they can state the degree of marbling, i.e. the size and distribution of lard enclosings in the meat, but only the lard thickness, cf. for instance Danish Pat. No. 109,246.

DISCLOSURE OF INVENTION

The object of the invention is to provide a process permitting such a sensitive measuring that the degree of marbling may be measured.

The process according to the invention is characterised by the light conducting means transmitting and receiving red light in a very narrow frequency band about a predetermined wave length, the signals transmitted being measured relative to a reference value automatically determined. The narrow band width renders it possible to avoid irrelevant signals from the surroundings. The automatic determination of a reference value implies an automatic adjustment as a consequence of the colour of the meat and the light of the surroundings. The apparatus is simplified due to the fact that manual adjustments are unnecessary.

Moreover according to the invention the wave length of the transmitter may be 0.93 $\mu m \pm 0.02$ $\mu m$, preferably 0.93 $\mu m \pm 0.01$ $\mu m$, and the receiver may be sensitive at 0.93 $\mu m$ too and be more broad-banded. In this manner the signal-to-noise-ratio is improved.

Furthermore according to the invention the light transmitted may be pulse modulated, whereby the signal-to-noise-ratio is additionally improved.

The pulse modulation may for instance be a coded pulse modulation.

Furthermore according to the invention, the reflection versus the penetration depth may be recorded in a memory, whereby a more comprehensive signal treatment of the values measured is permitted.

Finally according to the invention, the insertion of the probe may be performed in 256 steps, whereby the memory must comprise at least 256 locations, thus providing an appropriate resolving power.

BRIEF DESCRIPTION OF DRAWINGS

The invention will be described below with reference to the accompanying drawing, in which.

BEST MODE FOR CARRYING OUT THE INVENTION

Figure 1:
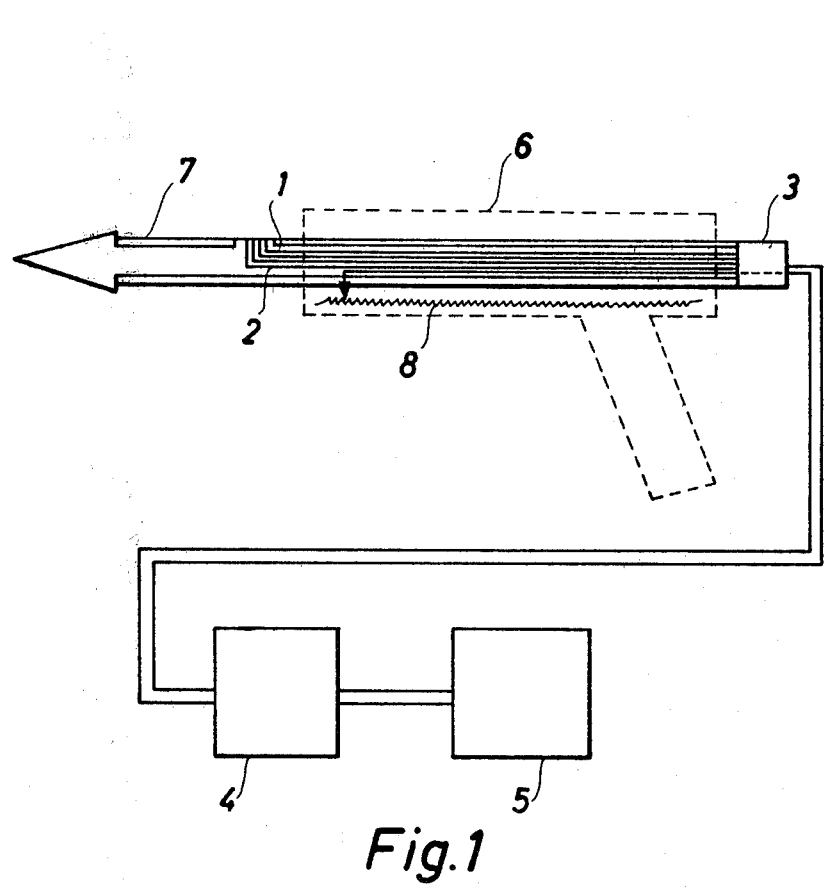
FIG. 1 illustrates a probe for carrying out the process according to the invention.

FIG. 1 illustrates a probe 7 to be introduced into a piece of meat. This probe is used for optically determining the meat-to-lard-ratio including the degree of marbling of the object. The probe comprising at least two light conducting means 1, 2 is introduced substantially perpendicular to the surface of the object. The light conducting means in the form of two light fibres 1, 2 open on to the side or at the spigot end of the probe 7. Through a converter 3 converting light signals into electrical signals, the fibres communicate with a calculating unit 4 recording the signal for the reflection in a memory 5. The location in the memory 5, which is recorded together with the reflection value, is dedetermined on the basis of the penetration depth x at the moment in question. The penetration depth stepwise registered may for instance be measured by means of a potentiometer 8 in the measuring instrument 6. The light fibers 1, 2 are adapted to transmit and receive red light in a very narrow frequency band about a predetermined wave length. In this manner irrelevant signals from the surroundings are excluded. Furthermore, the very narrow frequency band improves per se the signal-to-noise-ratio.

Figure 2:
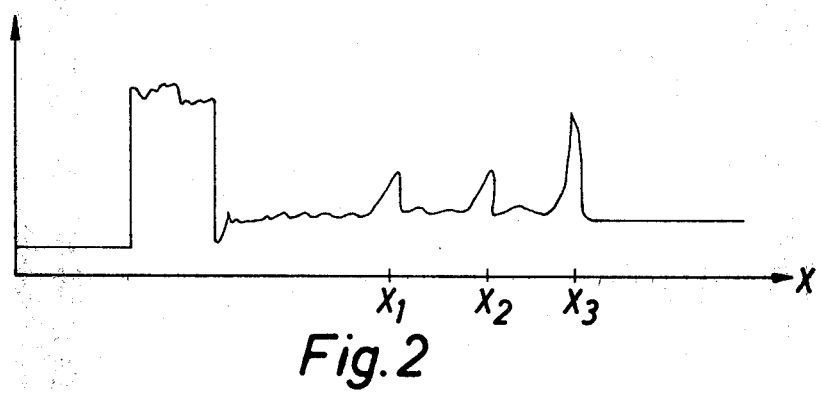
FIG. 2 illustrates the reflection as function of the insertion of the probe into a piece of meat.

The values recorded as function of the penetration depth x may for instance appear as illustrated in FIG. 2. The first portion of the curve illustrates the reflection outside the object. The next portion represents the layer of lard, whereas the final portion represents the layer of meat. The points of the meat reflection at $x_1$, $x_2$, and $x_3$ then correspond to lard enclosings. The principle is now that the calculating unit 4 receiving information concerning both the penetration depth and the reflection on the basis of a number of the lowest measured values automatically calculates a reference value. The lowest measured values are signals being for instance 10 times, optionally 5 times smaller than the greatest signals. The advantage by measuring the reflections relative to this reference value is that adjustments are saved, whereby the apparatus is less expensive and the measuring accuracy is improved. Furthermore, the colour of the meat, the light of the surroundings, and component aging phenomena, if any, are automatically compensated. The information disclosable after the signal treatment are first and foremost the degree of marbling, subsequently the location and size of the fatty tissues. The measuring process may be more sensitive by pulse modulating, optionally CPM-modulating the light transmitted.

The light diodes used are of the type TEXAS INSTRUMENTS TIL 23 or 24. These light diodes are sensitive at the wave length 0.93 $\mu m$, the band widths being 0.04 $\mu m$ and 0.02 $\mu m$, respectively. As receiver, a Si-photo transistor sensitive at the same frequency is employed.

The process and the apparatus according to the invention may be varied in many ways without deviating from the scope of the invention.

Figure 3:
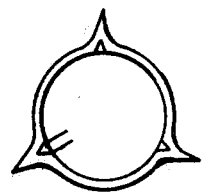
FIG. 3 is a rear view of a probe with three free cutting edges during the introduction, whereby furthermore the mouth of the light conducting means relative to the cutting edges is illustrated.

When the point of the probe penetrates the membranes separating the individual muscles and fatty tissues, cf. FIG. 3, the membranes may as a consequence of the friction between said membranes and the probe shaft be pressed downwards and thereby cover for the light transmitter and the receiver, said point of the probe being triangular and comprising three free cutting edges. Just opposite the three cutting edges, the membrane does not, however, abut the probe shaft, cf. FIG. 3, for which reason a location of the light means opposite a cutting edge is of a decisive importance, whereby the light means are equally axially positioned.

In other cases too, the light means may open on to the same axial position. As a result the measurements may be performed in the same plane. When the light means do not open on to the same plane perpendicular to the longitudinal axis of the probe, the degree of measurable layer thicknesses would be limited.

The probe 7 may for instance be of stainless steel.

We claim:

1. A process for optically evaluating the meat-to-lard-ratio in slaughtered animals or portions thereof, comprising:

inserting a probe comprising at least one light means including at least one transmitter transmitting light of a predetermined color and at least one receiver, said transmitter and receiver being located opposite or behind a cutting edge of said probe, substantially perpendicularly to a surface of a slaughtered animal or portion thereof, transmitting red light in a very narrow frequency band about a predetermined wave length, measuring reflected signals relative to a reference value automatically determined as the mean value of the lowest value in a series of received signals, and recording reflection versus penetration depth.

2. A process according to claim 1, wherein more than one light means is employed, said light means being located in substantially the same axial position.

* * * * *